United States Patent [19]
Cutler et al.

[11] Patent Number: 5,885,791
[45] Date of Patent: *Mar. 23, 1999

[54] ANTIFUNGAL AND ANTIBACTERIAL SUSCEPTIBILITY ASSAY

[75] Inventors: Jim E. Cutler; Marcia H. Riesselman, both of Bozeman, Mont.; Kevin C. Hazen, Afton, Va.

[73] Assignees: The Research and Development Institute, Inc., Bozeman, Mo.; The University of Virginia Patent Foundation, Charlottesville, Va.

[ * ] Notice: This patent issued on a continued prosecution application filed under 37 CFR 1.53(d), and is subject to the twenty year patent term provisions of 35 U.S.C. 154(a)(2).

[21] Appl. No.: 558,880

[22] Filed: Nov. 16, 1995

[51] Int. Cl.$^6$ .............................. C12Q 1/18; C12Q 1/28; C12Q 1/54

[52] U.S. Cl. .............................. 435/32; 435/14; 435/28; 435/975

[58] Field of Search .............................. 435/32, 14, 28, 435/975

[56] References Cited

U.S. PATENT DOCUMENTS

| | | |
|---|---|---|
| 3,216,907 | 11/1965 | Goldman . |
| 3,935,073 | 1/1976 | Waters . |
| 4,051,232 | 9/1977 | Protzman et al. . |
| 4,168,206 | 9/1979 | Boyer . |
| 4,254,220 | 3/1981 | Meiattini . |
| 4,259,442 | 3/1981 | Gayral . |
| 4,898,813 | 2/1990 | Albarella et al. . |
| 4,940,660 | 7/1990 | Hira et al. .................. 435/28 |
| 5,091,307 | 2/1992 | Escarguel et al. . |
| 5,212,066 | 5/1993 | Albarella et al. . |
| 5,312,762 | 5/1994 | Guiseppi-elie . |

OTHER PUBLICATIONS

Coleman et al., "New fluorescence assay for the quantitation of fungi", J. Clin. Microbiol., Vol. 27, pp. 2003–7, 1989.

Fisher et al., "Rapid microdilution–colorimetric assay for yeast susceptibility to fluorocytosine", Antimicrob. Agents Chemother., Vol. 12, pp. 614–617, 1977.

Hazen et al., "Potential use of the BacT/Alert automated blood culture system for antifungal susceptibility testing", J. Clin. Microbiol., vol. 32, pp. 848–850, 1994.

Hopfer et al., "Amphoteracin B susceptibility testing of yeasts with a Bactec radiometric system", Antimicrob, Agents Chemother., Vol. 11, pp. 277–280, 1977.

*Primary Examiner*—Gary L. Kunz
*Attorney, Agent, or Firm*—McDermott, Will & Emery

[57] ABSTRACT

An assay and test kit for testing and quantifying fungal inhibition by an antifungal agent. In the assay, inhibition is measured by a reduction in substrate uptake (such as glucose) as compared to uninhibited controls. A minimum inhibitory concentration value for each antifungal agent is obtained from the assay.

20 Claims, No Drawings

ANTIFUNGAL AND ANTIBACTERIAL SUSCEPTIBILITY ASSAY

The U.S. Government has a paid-up license in this invention and the right in limited circumstances to require the patent owner to license others on reasonable terms as provided for by the terms of NIH Grant No. 5-RO-1AI249412.

This invention was made with support under Grant No. 5R01 AI249412 (NIH) awarded by the National Institutes of Health.

TECHNICAL FIELD

The invention relates to an assay for testing and quantifying fungal or bacterial inhibition by an antifungal or antibacterial agent. The assay is also useful for testing mycobacteria and other anaerobic bacteria. In the assay, inhibition is measured by a reduction in substrate uptake (such as glucose) as compared to uninhibited controls. A minimum inhibitory concentration (MIC) value for each antifungal or antibacterial agent is obtained from the assay.

BACKGROUND ART

Methods have been described for antifungal susceptibility testing (reviewed in McGinnis and Rinaldi, 1991; Warnock, 1989; LaRocco, 1991; Pfaller and Rinaldi, 1993) [*see References section herein]. Several reports describe colorimetric methods for antifungal susceptibility testing. One method (Fisher and Armstrong, 1977) determines endpoints after 18 h of incubation by the change in a pH indicator as a result of the production of fungal metabolic acids. Other so-called colorimetric tests (McGinnis and Rinaldi, 1991) either determine cell turbidity at a specific visible light wavelength (Cheung et al., 1975) or measure power-time values with microcalorimetry (Beezer and Chowdhry, 1981).

A recent modification of the NCCLS (National Committees for Clinical Laboratory Standards, 1992) proposed standardized test for antifungal susceptibility testing of yeasts (document M27T) involves determination of endpoints by conversion of an oxidation-reduction chromogenic indicator (Pfaller et al., 1994; Pfaller and Barry, 1994). This colorimetric method has provided clearer endpoints for assessment of azole susceptibilities but still requires between 24 to 72 h for a final result. None of the methods involves direct measurement of substrate consumption.

U.S. Pat. No. 4,168,206 to Boyer discloses a method for testing the susceptibility of fungi to antifungal agents and comprises inoculating a non-nutrient agar with a fungus. A number of disks are impregnated with various types and concentrations of antifungal agents in the proper nutrient medium for the type of fungus and antifungal agent tested. The disk is placed upon the non-nutrient medium inoculated with the fungus. After an incubation period the plates are read to determine the minimum inhibitory concentration of the antifungal agent for the particular fungus.

U.S. Pat. No. 4,898,813 to Albarella et al. discloses catalytic test compositions and devices which are capable of generating different color hues at different analyte concentrations. The patent discloses analyte detection wherein the analyte may be glucose. An enzymatic reaction using glucose oxidase is involved. The presence of glucose is detected by a change in color hue.

U.S. Pat. No. 4,254,220 to Meiattini discloses a composition for the kinetic determination of glucose. The composition comprises glucose oxidase and peroxidase enzymes and determines the reaction velocity per concentration unit of glucose.

U.S. Pat. No. 5,091,307 to Escarguel et al. discloses a process characterized by enzymatic reactions which are carried out under anaerobic conditions between a liquid growth medium for mycoplasma containing a dilution medium of the sample of fluid to be analyzed, a first substrate which may be glucose in the presence of a color pH indicator, and a second substrate comprising glucose in the presence of a color indicator. The speed of the enzymatic response is followed while noting the time corresponding to the color change of the indicators. Colony counting is by light microscopy.

U.S. Pat. No. 5,212,066 to Albarella et al. discloses a diagnostic reagent system for the detection of substances which react with peroxidatively active substances resulting in the liberation of hydroperoxides. The reagent comprises a chromogenic oxidation indicator. The patent discloses that the reaction change of glucose with the enzyme glucose oxidase may be monitored.

U.S. Pat. No. 5,312,762 to Guiseppi-Elie discloses the measuring of the presence of an analyte such as glucose. Electrical resistance is measured in the absence and presence of the analyte. The reaction of glucose with glucose oxidase produces hydrogen peroxide which oxidizes a polymer film to make it more conductive. The background of the patent indicates that enzyme assays have been used to monitor therapeutic drugs.

U.S. Pat. No. 4,259,442 to Gayral discloses a method of rapid identification of different species of Streptococcus. A culture specimen is distributed in a certain number of capsules containing supporting disks impregnated with various reactive substrates. Cultures are incubated after which there is deposited on each of the supports a reagent which gives a colored product of reaction with the enzymatic degradation product or products of the substrate. The colors are observed and used to classify the bacterium as one of the Streptococcus groups.

U.S. Pat. No. 3,935,073 to Waters relates to a method and apparatus for detecting biological activity in which the presence of microorganisms is suspected. A growth medium is used containing radioactivity which when fermented produces a radioactive gaseous product. A fermentable carbon source such as glucose is broken down to form $CO_2$ during the growth of the bacteria. The content of radioactive $CO_2$ evolved is used to measure bacterial presence and growth in the medium.

U.S. Pat. No. 3,216,907 to Goldman relates to a rapid micromethod for determining the sensitivity of microorganisms to antimicrobial agents. Goldman used glucose detection to determine if bacterial agents in clinical specimens are inhibited by antibacterial drugs. For example, an antibiotic and a pH indicator are added to glucose broth prior to inoculation with the microorganism. The pH indicator will change its color as the pH of the medium drops only when the microorganism is not affected by the antibiotic. The patent indicates that in the presence of minute quantities of glucose, the enzyme glucose oxidase will immediately destroy the glucose to form gluconic acid and hydrogen peroxide. The liberated hydrogen peroxide reacts with a catalyst chromogen or glucose indicator to produce a blue to purple color.

The Goldman assay is not quantitative, thus, MIC determinations would be impossible. He uses infectious material from a patient as the inoculum. The number of infectious agents per sample in this assay are unknown and more than one kind of infectious agent may be present in infectious material. Both of these unknowns preclude quantitation and MIC determination from the Goldman assay.

Coleman et al. (1989) New fluorescence assay for the quantitation of fungi, J. Clin. Microbiol. 27:2003–2007 discloses the exposure of fungi to Fungiqual, a fluorescent stain. The fungi are quantified with a fluorometer which measures the fungiqual fluorescence intensity.

Fisher et al., (1977) Rapid microdilution-colorimetric assay for yeast susceptibility to fluorocytosine, Antimicrob. Agents Chemother. 12:614–617 discloses a yeast assay. The generation of acid by the yeast metabolism of glucose is measured by a change in color.

Hazen et al. (1994) discloses "Potential use of the BacT/Alert automated blood culture system for antifungal susceptibility testing", in J. Clin. Microbiol. 32:848–850. The BacT/Alert system detects growth of fungi or yeast on the basis of chromogenic change in a $CO_2$ sensitive indicator. The susceptibility of fungi or yeast to antifungal agents is measured with this system.

Hopfer et al. (1977) discloses "Amphotericin B susceptibility testing of yeasts with a Bactec radiometric system" in Antimicrob. Agents Chemother. 11:277–280. In the assay, the metabolism of glucose by yeast is measured by a decrease in a radiolabeled $CO_2$ production which is measured by a Bactec 225 automated bacterial detection system.

These tests differ from the present invention in several ways. First, no test is presently available that directly measures substrate consumption. Second, only a few tests require less than 24 h to obtain an endpoint and result. The known tests determine endpoints by methods that involve either direct determination of cell mass; cell viability by fluorescence; indirect determination of cell mass by calorimetry, ATP production, or radiometry. Third, rapid tests (<24 h) that have been developed require expensive equipment (Hazen et al., 1994; Beezar and Chowdhry, 1981; Green et al., 1994; Coleman et al., 1989; Anselm and Nilsson, 1984; Hopfer and Groeschel, 1977; Hopfer et al., 1979). Most other published assays utilize reduced fungal growth as the indicator of antifungal activity. Many other methods require either a minimum of two days for results or expensive instrumentation and none measure lethality of the antifungal or antibacterial agent.

The fungal/antimicrobial susceptibility assay of the invention overcomes the deficiencies of prior art fungal susceptibility assays by providing for an assay which measures minimum inhibitory concentration, and can be performed in about 8 hours or less and which involves inexpensive reagents and requires only modest, common clinical laboratory equipment.

DISCLOSURE OF THE INVENTION

An object of the invention is to provide an antifungal and antibacterial susceptibility assay which can be performed in 8 hours or less.

Another object of the invention is to provide an antifungal or antibacterial susceptibility assay which provides minimum inhibitory concentration and minimum lethal dose information.

An object of the invention is to provide an anti-fungal susceptibility assay comprising the steps of, a) adding sample antifungal or antibacterial agents to a vessel;

b) adding fungal inoculum to said vessel;

c) adding glucose to the vessel of step (b) to grow a culture of said fungal inoculum;

d) incubating said culture for a sufficient amount of time to allow fungal inoculum or bacterial inoculum to grow;

e) mixing a colorizing agent without glucose oxidase to a control fungal or bacterial culture;

f) adding glucose oxidase with colorizing agent to fungal or bacterial cultures of step (d);

g) incubating said fungal or bacterial cultures of step (f) with glucose oxidase for a time sufficient to develop said colorizing agent; and h) quantifying the amount of color development in each sample to determine the minimum inhibitory concentration of sample antifungal or antibacterial agent, as compared to said control.

A still further object of the invention is to provide for an anti-fungal susceptibility assay kit.

The above and other objects of the invention will become readily apparent to those of skill in the relevant art from the following detailed description and figures, wherein only the preferred embodiments of the invention are shown and described, simply by way of illustration of the best mode of carrying out the invention. As is readily recognized the invention is capable of modifications within the skill of the relevant art without departing from the spirit and scope of the invention.

DESCRIPTION OF THE INVENTION

The fungal susceptibility assay of the invention involves the measurement of fungal or microbial inhibition by an antifungal and antimicrobial agent as a reduction in substrate uptake as compared to uninhibited controls. The assay is also appropriate for testing antimicrobial agents against bacteria such as the *Mycobacterium tuberculosis* complex group organisms and other mycobacterial species (such as *M. avium-intracellulare* complex, *M. fortuitum*, *M. smegatis* and *M. kanassi*), and other aerobic bacteria (such as Gram positive bacteria and Gram negative bacteria). The assay format is appropriate for testing antimicrobial agents against diseases caused by culturable protozoa.

At least two advantages of the present assay approach are speed and low expense of the assay. The assay may be performed to completion within a normal working day and at low cost in terms of equipment and technician time and training as elaborated below.

The assay advantageously requires only a minimum of technical knowledge about fungi. This advantage makes the assay useful to virtually all clinical microbiologists. Currently, most antifungal susceptibility testing is done only at specialty reference laboratories. The present assay does not require a technologist dedicated to antifungal and antibacterial susceptibility testing. That is, the assay includes several incubations during which time the technologist may carry out other unrelated duties.

A major objective of the assay is to provide clinical laboratories with a rapid method for antifungal and antibacterial MIC determination. A minimum inhibitory concentration (MIC) is a quantitative value which gives the actual concentration of drug that inhibits a given fungus or microbe from growing. To fulfill this objective, the assay is quantitative with respect to the number of fungal or microorganisms used in the assay and the purity of organisms tested. These criteria must be met for an MIC result to be valid. The assay is run on a known number of fungi obtained in pure culture and is thus quantitative, and can be used for MIC determinations. Specimen fungal cultures may be purified by standard microbiological purification techniques. These techniques are outlined in W. W. Koneman, S. D. Allen, W. M. Janda, P. C. Schreckenberger and W. C. Winn. 1992. *Color Atlas and Textbook of Diagnostic Microbiology*. 4th Ed., Chap. 1, J. B. Lippincott Co., Philadelphia, or as outlined in Maniatis et al., *Molecular Cloning: A Laboratory Manual*, Cold Spring Harbor Press (1989) incorporated by reference herein in its entirety.

In a preferred embodiment, the assay utilizes glucose as the growth substrate. Glucose is essentially a universal growth substrate for fungi and is the most preferred for this assay. Any fungal or microbial energy, carbon or nitrogen source may be used as the fungal substrate. Other fungal substrates include, but are not limited to, for example, acetate, galactose, ammonia/ammonium and glycerol. Glucose is metabolized in the assay by glucose oxidase. An indicator of glucose concentration or cellular metabolic activity is used to obtain the MIC of antifungal and antibacterial drugs against various fungi. Other methods for glucose detection can be used, such as potentiometric methods (e.g., ion specific probes).

If fungal substrates other than glucose are used, the appropriate enzyme which metabolizes the substrate is used. For example, if galactose is chosen as the substrate, galactose oxidase is used as the enzyme in the assay. If an ammonium salt is used in the assay, L-glutamate dehydrogenase or a potentiometric method is be used. Preferably, fungi that grow primarily as non-dematiaceous yeasts are tested. The assay is readily adapted to use with other yeasts and with filamentous fungi. The assay, in a preferred embodiment is accommodated for robotic automation.

The assay below represents a preferred embodiment of performing the assay of the invention.

EXAMPLE 1

1. Pipette 50 µl per well of the test antifungal dilutions (prepared 3× in RPMI 1640 (Sigma) without glucose) into the appropriate wells of a 96 well microtiter plate (Corning #25880-96).
2. Pipette 50 µl per well of RPMI 1640 with 2 mg/ml glucose.
3. Pipette 50 µl per well of the yeast inoculum (prepared 3× in RPMI 1640 without glucose) into the appropriate wells of the plate.
4. Tap the plate gently to mix. Cover the plate and preincubate at 37° C. for 0 to 6 hours.
5. Add 50 µl/well of RPMI 1640 with 1 mg/ml glucose.
6. Tap the plate gently to mix. Cover the plate and return it to the 37° C. incubator for 3 hours.
7. Add 50 µl of color mix without glucose oxidase to each background control well.
8. Add glucose oxidase to the remaining color mix. Mix.
9. Add 50 µl of complete color mix to each test well. Tap the plate gently to mix.
10. Develop for 30 minutes at room temperature.
11. Read O.D. at 540–570 nm in microplate spectrophotometric reader.
12. Net O.D./well=(O.D. sample with glucose oxidase) —(O.D. sample without glucose oxidase).

In the above method, preincubation allows the yeast to establish metabolism in the presence of the antifungal agents prior to the glucose assay. Glucose is then added back to the culture, and the differential uptake of this glucose is measured after three hours. Preincubation (steps 4 and 5) is optional depending on the fungus and antifungal agent combination.

Drug treated samples are compared to control (untreated) samples for glucose uptake. Fungal or microbial susceptibility to the drug is indicated by a decrease in glucose uptake by the treated samples.

EXAMPLE 2

Same as example 1, except a strain of *Torulopsis glabrata* is tested with amphotericin B as the antifungal agent.

EXAMPLE 3

Same as example 1, except a strain of *Torulopsis glabrata* is tested with fluconazole as the antifungal agent.

EXAMPLE 4

Same as example 1, except a strain of *Candida albicans* is tested with amphotericin B as the antifungal agent.

EXAMPLE 5

Same as example 1, except a strain of *Candida albicans* is tested with fluconazole as the antifungal agent.

EXAMPLE 6

Same as example 1, except a strain of *Cryptococcus neoformans* is tested with fluconazole and amphotericin B as antifungal agents in yeast nitrogens base (YNB) instead of RPMI 1640.

EXAMPLE 7

Same as example 1, except a strain of *Aspergillus fumigatus*, a mould, is tested with amphotericin B.

EXAMPLE 8

Same as example 1, except an ammonium salt is substituted for the glucose as a detectable growth substrate.

EXAMPLE 9

Same as example 1, except galactose is substituted for the glucose fungal substrate and galactose oxidase is substituted for glucose oxidase.

EXAMPLE 10

An alternative embodiment of the anti-bacterial susceptibility assay comprises the steps of,
  a. pipetting 50 µl per well of the test anti-bacterial dilutions into wells of a 96 well microtiter plate;
  b. pipetting 50 µl per well of RPMI 1640 with 2 mg/ml glucose;
  c. pipetting 50 µl per well of the bacterial inoculum (prepared 3× in RPMI 1640 without glucose) into the wells of the plate;
  d. tapping the plate gently to mix;
  e. covering the plate and preincubate at 37° C. for 0 to 19 hours;
  f. adding 50 µl/well of RPMI 1640 with 2 mg/ml glucose;
  g. tapping the plate gently to mix;
  h. covering the plate and return it to the 37° C. incubator for 3 hours;
  i. adding 50 µl of color mix without glucose oxidase to each background control well;
  j. adding glucose oxidase to the remaining color mix;
  k. adding 50 µl of complete color mix to each test well;
  l. developing for 30 minutes at room temperature; and
  m. reading the optical density at 540–570 nm with a 655 nm reference filter at dual wavelength.

Thus, an anti-fungal/antimicrobial susceptibility assay in accordance with the invention generally comprises the steps of, a) adding sample antifungal agents to a vessel;

b) adding fungal inoculum to said vessel;

c) adding glucose to the vessel of step (b) to grow a culture of said fungal inoculum;

d) incubating said culture for a sufficient amount of time to allow fungal inoculum to grow;

e) adding additional glucose substrate;

f) incubating for an amount of time sufficient to allow substrate uptake;

g) mixing a colorizing agent without glucose oxidase to a control fungal culture;

h) adding glucose oxidase with colorizing agent to fungal cultures of step (f);

i) incubating said fungal cultures of step (h) with glucose oxidase for a time sufficient to develop said colorizing agent; and j) quantifying the amount of color development present in each sample to determine the minimum inhibitory concentration of sample antifungal agent, as compared to said control.

To avoid starvation conditions, the yeast may be suspended in a complete nutrient medium, then pelleted and suspended in the assay medium at the appropriate concentration for mixture with the antifungal agents.

In the assay, the incubation time to allow fungal inoculum to grow in the presence of glucose and the antifungal agent may be selected from 0 to about 8 hours. In a preferred embodiment the incubation time is about 3 hours.

The most rapid result can be achieved by the assay of the invention in about 3.5 hours. In an alternative assay, the total assay can be performed in 8 hours or less. One of skill in the art knows that incubation times are dependent on fungal species metabolism, and adjustment of incubation time can be made according to fungal species. Examples discussed herein which are relevant to fungi are also relevant to antimicrobial testing.

The assay vessel is preferably a microtiter plate well, however, a dipstick or nitrocellulose membrane may alternatively be used.

In the present assay, glucose serves as the metabolic substrate. However, the assay will work well with other metabolic substrates, such as galactase or ammonium.

The colorizing agent, 4-amino antipyrine and N-ethyl-N-sulfopropyl-m-toluidine, turns purple upon conversion of glucose to $H_2O_2$ and further interaction with horseradish peroxidase. Other colorizing agents which can be used include: (1) ABTS (2,2'-azinodi [ethylbenzothiozoline] sulfonate; (2) 0-phenylenediamine; or (3) 3,3',5,5'tetramethylbenzene.

Preferably, about 25–50 microliters of colorizing agent is used. In a most preferred embodiment of the invention 50 microliters of colorizing agent is used. The preferred time to develop said colorizing agent is about 30 min.

Preferably, about 25–50 microliters of fungal inoculum is used. In a most preferred embodiment of the invention 50 microliters of fungal inoculum is used.

Any anti-fungal agent may be tested using the assay of the invention. In a preferred embodiment the antifungal agent is selected from azoles (e.g., fluconazole or itraconazole), polyenes (e.g., amphotericin B), metabolic analogs (e.g., 5-fluorocytosine), cell wall inhibitors (e.g., nikkomycins, eichinocandins, polyonins) and allylamines (e.g., terbinefine).

The step of quantitating the amount of color development is performed on a microplate reader which provides a value for the minimum inhibitory concentration of the antifungal agent. In a preferred embodiment the microplate reads O.D. at 540–570 nm.

Thus the assay of the invention may be completed in 8 hours or less and with some fungi-drug combinations it may be completed in 3.5 hours or less. In addition, the assay has objective endpoints.

In another embodiment of the invention the assay involves the following 11 steps. 1) Adding test antifungal dilutions to microtiter plate wells. 2) Adding glucose to the wells. 3) Adding fungal inocula dilutions to the wells. 4) Gently mixing the mixture. 5) Mixing and incubating for three hours. 6) Mixing color mix without glucose oxidase to each background control well. 7) Adding glucose oxidase to color mix. 8) Adding color mix to each test well. 9) Developing for 30 minutes. 10) Obtaining an MIC value or MLD value. 11) Compare control vs. treated samples for degree of inhibition (i.e., MFC) of glucose uptake.

In a preferred embodiment of the invention the assay utilizes (but is not restricted to) microtiter plates, reagents in solution and an ELISA plate reader to determine the color results.

The assay may be modified to provide minimum fungicidal concentration (MFC) information and results. It is often critical to determine whether an antifungal agent is fungicidal or whether it is merely fungistatic. This determination influences the course of treatment for the patient. To determine MFC's, fungal cells may be stained while in the wells or the cells can be removed from the wells after the MIC determination and stained for viability. Examples of viability stains include FUNGOLIGHT and YO-PRO, available from Molecular Probe.

For several reasons, the use of filter pads, to which the fungal cells may adhere, and infectious material as the inoculum would compromise the ability to determine fungal viability. Thus filter pads should not be used as an assay substrate.

The present assay utilizes a chemically defined medium which allows standardization of the assay. Assays such as those of Goldman, preincubate the medium with a known microbe to deplete traces of glucose. This step may confound subsequent results of the assay.

In the assay of the invention, the antifungal drugs are added in solution or suspension, thus assuring an interaction with the fungi. This factor unexpectedly provides a benefit over known assays, such as the Goldman assay, in which the drugs are first adhered to a filter pad and the infectious material is added to the top of the pad. The Goldman assay does not work with water insoluble antifungal agents, hydrophobic/non-soluble antifungals (important ones, such as amphotericin B and itraconazole) which stay in the filter pad and do not have a chance to interact with the fungi.

The invention also provides for a test kit for minimum inhibitory concentration, anti-fungal susceptibility testing. Such a test kit in accordance with the invention may comprise a) a microtiter plate, b) sample anti-fungal agents, pre-diluted, c) diluent, d) colorizing agent, e) fungal metabolic substrate, such as glucose, and f) metabolic enzyme, such as glucose oxidase.

A microtiter plate ELISA reader which is normally present in a lab can be used to detect and quantify the MLD and MIC values. The kit may also include instructions for use. The test fungal inoculum must be supplied by the technician from a specimen, which in a preferred embodiment is taken from a patient. The specimen is purified prior to performance of the assay. This assay is adaptable to robotics technology.

References

1. Anselm, S. and L. Nilsson (1984) Direct membrane-damaging effect of ketoconazole and tioconazole on *Candida albicans* demonstrated by bioluminescent assay of ATP. *Antimicrob. Agents Chemother.* 26:22–25.
2. Beezer, A. E. and B. Z. Chowdhry (1981) Flow microcalorimetric bioassay of polyene antibiotics: interaction with growing *Saccharomyces cerevisiae. Experientis* 37:828–831.
3. Cheung, S. C., G. Medoff, D. Schlessinger and G. S. Kobayashi (1975) Stability of amphotericin B in fungal culture media. *Antimicrob. Agents Chemother.* 8:426–428.
4. Coleman, T., J. V. Madassery, G. S. Kobayashi, M. H. Nahm and J. R. Little (1989) New fluorescence assay for the quantitation of fungi. *J. Clin. Microbiol.* 27:2003–2007.
5. Fisher, B. D. and D. Armstrong (1977) Rapid microdilution-colorimetric assay for yeast susceptibility to fluorocytosine. *Antimicrob. Agents Chemother.* 12:614–617.
6. Green, L., B. Petersen, L. Steimel, P. Haeber and W. Current (1994) Rapid determination of antifungal activity by flow cytometry. *J. Clin. Microbiol.* 32:1088–1091.
7. Hazen, K. C., M. P. Chery and Y. Han (1994) Potential use of the BacT/Alert automated blood culture system for antifungal susceptibility testing. *J. Clin. Microbiol.* 32:848–850.
8. Hopfer, R. L. and D. Groeschel (1977) Amphotericin B susceptibility testing of yeasts with a Bactec radiometric system. *Antimicrob. Agents Chemother.* 11:277–280.
9. Hopfer, R. L., K. Mills, and D. Groeschel (1979) Radiometric method for determining the susceptibility of yeasts to 5-fluorocytosine. *Antimicrob. Agents Chemother.* 15:313–314.
10. LaRocco, M. (1991) Recent developments in antifungal susceptibility testing. *Clin. Microbiol. Newsletter.* 13:81–85.
11. McGinnis, M. R. and M. G. Rinaldi (1991) Antifungal drugs: mechanisms of action, drug resistance, susceptibility testing, and assays of activity in biological fluids. In V. Lorian (Ed.), Antibiotics in Laboratory Medicine, 3d Edn., Williams and Wilkins, Baltimore, pp. 198–257.
12. National Committee for Clinical Laboratory Standards (1992) Reference method for broth dilution antifungal susceptibility testing of yeasts; proposed standard. M27-P, National Committee for Clinical Laboratory Standards, Villanova.
13. Pfaller, M. A. and A. L. Barry (1994) Evaluation of a novel colorimetric broth microdilution method for antifungal susceptibility testing of yeast isolates. *J. Clin. Microbiol.* 32:1992–1996.
14. Pfaller, M. A., Q. Vu, M. Lancaster, A. Espinel-Ingroff, A. Fothergill, C. Grant, M. R. McGinnis, L. Pasarell, M. G. Rinaldi and L. Steele-Moore (1994) Multisite reproducibility of colorimetric broth microdilution method for antifungal susceptibility testing of yeast isolates. *J. Clin. Microbiol.* 32:1625–1628.
15. Pfaller, M. A. and M. G. Rinaldi (1993) Antifungal susceptibility testing: current state of technology, limitations, and standardization. *Infect. Dis. Clin. North America.* 7:435–444.
16. Warnock, D. W. (1989) Antifungal drug susceptibility testing. *Curr. Top. Med. Mycol.* 3:403–416.

The purpose of the above description and examples is to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A quantitative method of determining antimicrobial susceptibility comprising the steps of,
    a) adding sample antimicrobial agents to a vessel;
    b) adding microbial inoculum comprising microbes of a predetermined amount and a single identity to said vessel, thereby permitting immediate interaction between said antimicrobial agents and said microbial inoculum;
    c) adding microbial metabolic substrate comprising a microbial energy, carbon or nitrogen source to the vessel of step (b) to grow a culture of said microbial inoculum;
    d) incubating said culture for a sufficient amount of time to allow microbial inoculum to grow;
    e) adding enzyme specific for said microbial metabolic substrate with colorizing agent to microbial cultures of step (d);
    f) incubating said microbial cultures of step (e) with enzyme specific for said microbial metabolic substrate for a time sufficient to develop said colorizing agent; and
    g) quantifying the amount of colorizing agent present in each sample to determine the minimum inhibitory concentration of sample antimicrobial agent.

2. A quantitative method of determining anti-fungal susceptibility comprising the steps of,
    a) adding sample antifungal agents to a vessel;
    b) adding fungal inoculum comprising fungi of a predetermined quantity and a single identity to said vessel, thereby permitting immediate interaction between said antifungal agents and said fungal inoculum;
    c) adding fungal metabolic substrate comprising a fungal energy, carbon or nitrogen source to the vessel of step (b) to grow a culture of said fungal inoculum;
    d) incubating said culture for a sufficient amount of time to allow fungal inoculum to consume substrate;
    e) adding enzyme specific for said fungal metabolic substrate with colorizing agent to fungal cultures of step (d);
    f) incubating said fungal cultures of step (f) with enzyme specific for said fungal metabolic substrate for a time sufficient to develop said colorizing agent; and
    g) quantifying the amount of colorizing agent present in each sample to determine the minimum inhibitory concentration of sample antifungal agent.

3. The assay of claim 2, further comprising, after step (a), adding metabolic substrate to said vessel.

4. The assay of claim 2, further comprising, after step (h), removing fungal inoculum from vessel and applying a fungal viability stain or applying viability stain directly to vessel, to determine whether the antifungal agent is fungicidal or fungistatic.

5. The assay of claim 2, wherein said vessel is a microtiter plate well.

6. The assay of claim 2, wherein said fungal inoculum is yeast.

7. The assay of claim 6, wherein said yeast is *Candida albicans*.

8. The assay of claim 2, wherein said colorizing agent is horseradish peroxidase with 4-amino antipyrine and N-ethyl-N-sulfopropyl-m-toluidine.

9. The assay of claim 8 wherein said colorizing agent is about 50 microliters and said glucose is 50 microliters.

10. The assay of claim 8 wherein said time to develop said colorizing agent is about 30 min.

11. The assay of claim 2, wherein said fungal inoculum is *Torulopsis glabrata*.

12. The assay of claim 2, wherein said anti-fungal agent is selected from the group consisting of azoles, polyenes, metabolic analogs, cell wall inhibitors and allylamines.

13. The assay of claim 2, wherein said step of quantifying the amount of colorizing agent is performed on a microplate reader.

14. The assay of claim 2, wherein said microplate reader O.D. is read at 540–570 nm.

15. The assay of claim 2, wherein said incubation time is from 0 to about 6 hours.

16. The assay of claim 2, wherein said incubation time is about 3 hours at 37 degrees.

17. The assay of claim 2, wherein said assay is completed in about 3.5 hours or less.

18. The assay of claim 2, wherein said assay is completed in about 8.0 hours or less.

19. The assay of claim 1, wherein said antimicrobial assay is an antifungal assay.

20. A quantitative method of determining anti-fungal susceptibility comprising the steps of,
   a. pipetting 50 µl per well of the test antifungal dilutions into wells of a 96 well microtiter plate;
   b. pipetting 50 µl per well of RPMI 1640 with 2 mg/ml glucose;
   c. pipetting 50 µl per well of the fungal inoculum dilutions comprising fungi of a predetermined quantity and a single identity (prepared 3× in RPMI 1640 without glucose) into the wells of the plate, thereby permitting immediate interaction between said antifungal agents and said fungal inoculum;
   d. tapping the plate gently to mix;
   e. covering the plate and preincubate at 37° C. for 0 to 6 hours;
   f. adding 50 µl/well of RPMI 1640 with 2 mg/ml glucose;
   g. tapping the plate gently to mix;
   h. covering the plate and return it to the 37° C. incubator for 3 hours;
   i. adding 50 µl of complete color mix to each test well;
   j. developing for 30 minutes at room temperature; and
   k. reading the optical density at 540–570 nm to determine the minimum inhibitory concentration of sample antifungal agent, as compared to said control.

* * * * *